(12) United States Patent
Epstein et al.

(10) Patent No.: US 6,906,166 B2
(45) Date of Patent: Jun. 14, 2005

(54) POLYMERS AND OLIGOMERS, THEIR SYNTHESIS, AND ELECTRONIC DEVICES INCORPORATING SAME

(75) Inventors: Arthur J. Epstein, Columbus, OH (US); Daike Wang, Duncan, SC (US)

(73) Assignee: The Ohio State University, Columbus, OH (US)

(*) Notice: Subject to any disclaimer, the term of this patent is extended or adjusted under 35 U.S.C. 154(b) by 0 days.

(21) Appl. No.: 10/847,896

(22) Filed: May 18, 2004

(65) Prior Publication Data

US 2005/0027097 A1 Feb. 3, 2005

Related U.S. Application Data

(62) Division of application No. 10/084,866, filed on Feb. 28, 2002, now Pat. No. 6,777,532.
(60) Provisional application No. 60/275,762, filed on Mar. 14, 2001, and provisional application No. 60/275,443, filed on Mar. 13, 2001.

(51) Int. Cl.[7] .............................................. C08G 73/06
(52) U.S. Cl. ....................... 528/423; 528/423; 528/212; 528/230; 528/242; 528/244; 528/425; 525/88
(58) Field of Search ................................. 528/423, 212, 528/23, 242, 244, 425; 525/88

(56) References Cited

U.S. PATENT DOCUMENTS

| | | | |
|---|---|---|---|
| 5,147,968 A | 9/1992 | Epstein et al. | 528/210 |
| 5,294,694 A | 3/1994 | Epstein et al. | 528/210 |
| 5,463,014 A | 10/1995 | Epstein et al. | 528/210 |
| 5,663,573 A | 9/1997 | Epstein et al. | 257/40 |
| 5,858,561 A | 1/1999 | Epstein et al. | 428/690 |
| 5,955,834 A | 9/1999 | Epstein et al. | 313/501 |
| 6,004,681 A | 12/1999 | Epstein et al. | 428/457 |
| 6,207,301 B1 | 3/2001 | Ohnishi et al. | 428/690 |
| 6,403,236 B1 | 6/2002 | Ohnishi et al. | 428/690 |
| 6,403,237 B1 | 6/2002 | Noguchi et al. | 428/690 |
| 6,414,104 B1 | 7/2002 | Pei | 528/86 |
| 6,445,126 B1 | 9/2002 | Arai et al. | 313/504 |
| 6,495,273 B1 | 12/2002 | Hwang et al. | 428/690 |

OTHER PUBLICATIONS

Z. Yang, I. Sokolik, and F. E. Karasz, "A Soluble Blue–Light Emitting Polymer", *Macromolecules* 1993, 26, 1188–1190.

*Primary Examiner*—Duc Truong
(74) *Attorney, Agent, or Firm*—Standley Law Group LLP

(57) ABSTRACT

The invention relates to polymers and oligomers, methods of their synthesis, and electronic devices comprising them.

12 Claims, No Drawings

POLYMERS AND OLIGOMERS, THEIR SYNTHESIS, AND ELECTRONIC DEVICES INCORPORATING SAME

This application is a divisional application of U.S. application Ser. No. 10/084,866, filed Feb. 28, 2002, now U.S. Pat. No. 6,777,532, which claims the priority of U.S. Provisional Application Ser. No. 60/275,762, filed Mar. 14, 2001 and U.S. Provisional Application Ser. No. 60/275,443, filed Mar. 13, 2001.

TECHNICAL FIELD

The invention relates to polymers and oligomers, methods of their synthesis, and electronic devices comprising them.

BACKGROUND OF THE INVENTION

The present invention is directed to polymeric compositions useful in producing electronic devices. It is an object of the present invention to produce stable compositions capable of functioning in a wide variety of electronic devices.

Novel features and advantages of the present invention, in addition to those mentioned above, will become apparent to those skilled in the art from a reading of the following description or from practice of the invention.

SUMMARY OF THE INVENTION

The present invention includes compositions of matter including polymers, oligomer and their constituent monomeric units. The present invention also includes methods of making the compositions and devices made therefrom.

Polymer 1

The present invention includes a composition of matter comprising a polymer of the general structure:

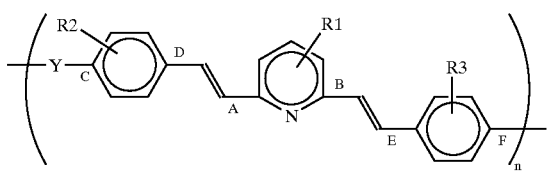

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; wherein bonds A and B may independently be either ortho, meta or para with respect to the pyridyl nitrogen; wherein bonds C and D may be either ortho, meta or para with respect one another; and wherein bonds E and F may be either ortho, meta or para with respect one another; wherein Y may be a moiety selected from the group consisting of $-(CH_2)_x-$, $-(CH_2)_xO-$, $-O(CH_2)_x-$ and $-O(CH_2)_xO-$ wherein x is an integer in the range of 1 to 15 inclusive; and wherein n is an integer greater than 1.

The R2 substituent is preferably a methoxy group with most preferably at least two R2 substituents being methoxy groups. The R3 substituent is preferably a methoxy group with most preferably at least two R3 substituents being methoxy groups.

It is preferred that the vinyl linkages A and B attach at positions ortho to the pyridyl nitrogen. It is also preferred that bonds C and D be para with respect one another, and that E and F be para with respect one another.

It Is also preferred that x be an integer in the range of 1 to 6 inclusive.

Polymer 2

The present invention includes a composition of matter comprising a polymer of the general structure:

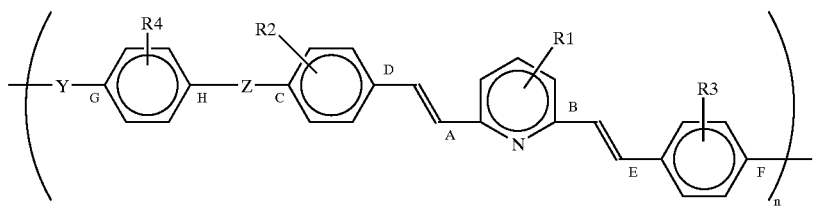

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; wherein bonds A and B may independently be either ortho, meta or para with respect to the pyridyl nitrogen; wherein bonds C and D may be either ortho, meta or para with respect one another; wherein bonds E and F may be either ortho, meta or para with respect one another; wherein bonds G and H may be either ortho, meta or para with respect one another; wherein Y may be a moiety selected from the group consisting of $-(CH_2)_x-$, $-(CH_2)_xO-$, $-O(CH_2)_x-$ and $-O(CH_2)_xO-$ wherein x is an integer in the range of 1 to 15 inclusive; wherein Z may be a moiety selected from the group consisting of $-(CH_2)_x-$, $-(CH_2)_xO-$, $-O(CH_2)_x-$ and $-O(CH_2)_xO-$ wherein x is an integer in the range of 1 to 15 inclusive; and wherein n is an integer greater than 1.

The R1, R2, R3 and R4 substituents preferably are methoxy groups with most preferably at least two of the R1, R2, R3 and R4 substituents being methoxy groups.

It is preferred that the vinyl linkages A and B attach at positions ortho to the pyridyl nitrogen. It is also preferred that bonds C and D be para with respect one another, and that E and F be para with respect one another.

It Is also preferred that x be an integer in the range of 1 to 6 inclusive.

Oligomers 1, 2, 3 & 4

The present invention includes a composition of matter comprising an oligomer of the general structure:

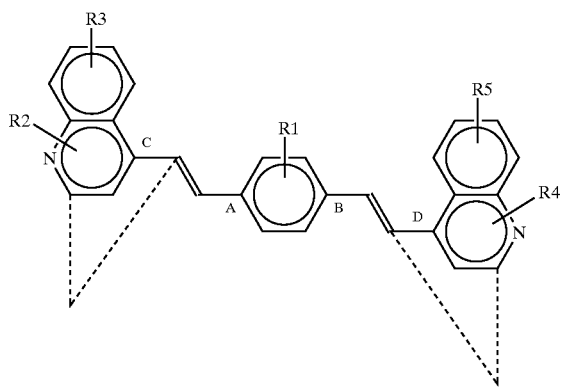

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; wherein bonds A and B may be either ortho, meta or para from one another; wherein bond C may be either ortho, meta or para with respect to the respective quinoyl nitrogen as indicated by the dotted lines; and wherein bond D may be either ortho, meta or para with respect to the respective quinoyl nitrogen as indicated by the dotted lines.

The R1, R2, R3, R4, and R5 substituents preferably are methoxy groups with most preferably at least two of the R1, R2, R3, R4, and R5 substituents being methoxy groups.

It is preferred that the vinyl linkages A and B attach at positions para to one another.

Oligomer 5, 6, 7 & 8

A composition of matter comprising an oligomer of the general structure:

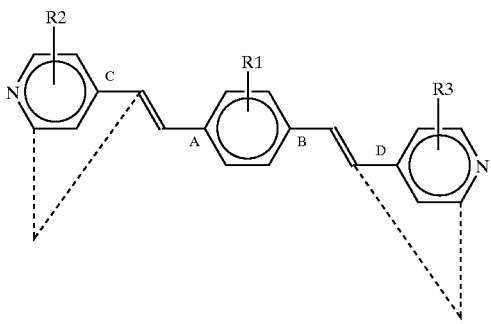

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; wherein bonds A and B may independently be either ortho, meta or para from one another; wherein bond C may be either ortho or para with respect to the respective pyridyl nitrogen as indicated by the dotted lines; and wherein bond D may be either ortho or para with respect to the respective pyridyl nitrogen as indicated by the dotted lines.

The R1, R2 and R3 substituents preferably are methoxy groups with most preferably at least two of the R1, R2 and R3 substituents being methoxy groups.

It is preferred that the vinyl linkages A and B attach at positions para to one another.

Oligomers 9 & 10

The present invention also includes a composition of matter comprising an oligomer of the general structure:

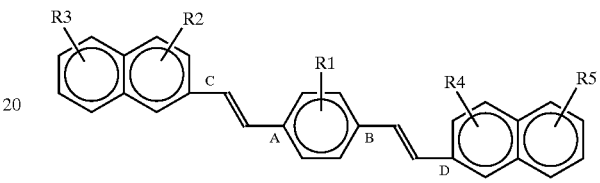

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; wherein bonds A and B may independently be either ortho, meta or para from one another.

Bonds C and D may attach at any position onto rings R2/R3 and R4/R5, respectively, although it iis preferred that they attach as shown above.

The R1 substituent preferably is a methoxy group with most preferably at least two of the R1 substituents being methoxy groups.

Oligomers 11, 12 & 13

The present invention also includes a composition of matter comprising an oligomer of the general structure:

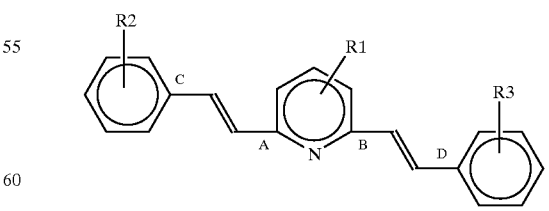

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; and wherein bonds A and B may independently be either ortho, meta or para from the pyridyl nitrogen.

The R1, R2 and R3 substituents preferably are methoxy groups with most preferably at least two of the R1, R2 and R3 substituents being methoxy groups. Three of the R2 and R3 substituents may also preferably be methoxy groups.

Polymer 6, 7, 8, & 9

A composition of matter comprising a polymer of the general structure:

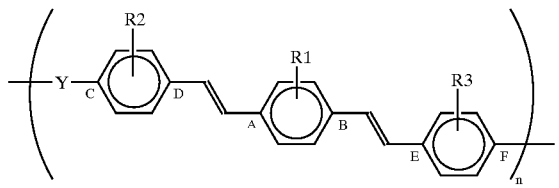

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; wherein bonds A and B may be either ortho or para with respect one another; wherein bonds C and D may be either ortho or para with respect one another; wherein bonds E and F may be either ortho or para with respect one another; wherein Y may be a moiety selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; and wherein n is an integer greater than 1.

The R1, R2 and R3 substituents preferably are methoxy groups with most preferably at least two of the R1, R2 and R3 substituents being methoxy groups.

The present invention includes a number of block co-polymer compositions derived from the oligomers described above.

Block Co-polymer of Oligomers 1, 2, 3 & 4 (Y Only)

The present invention also includes a composition of matter comprising a block co-polymer of the general structure:

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; wherein bonds A and B may independently be either ortho, meta or para from one another; wherein bond C may be either ortho, meta or para with respect to the respective quinoyl nitrogen; and wherein bond D may be either ortho, meta or para with respect to the respective quinoyl nitrogen; wherein Y may be a moiety attached at any point on rings R2 and R3, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; and wherein n is an integer greater than 1.

These block co-polymers may have geometries and substituents as do the oligomers from which they are derived, as described above.

Block Co-polymer of Oligomers 1, 2, 3 & 4 (Y, R & Z)

The present invention also includes a composition of matter comprising a block co-polymer of the general structure:

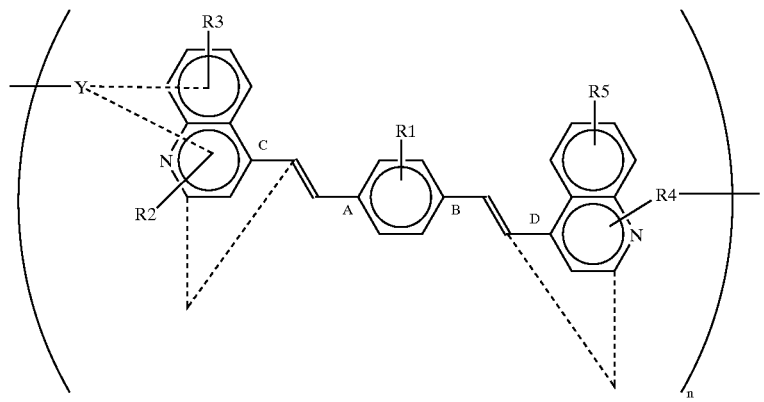

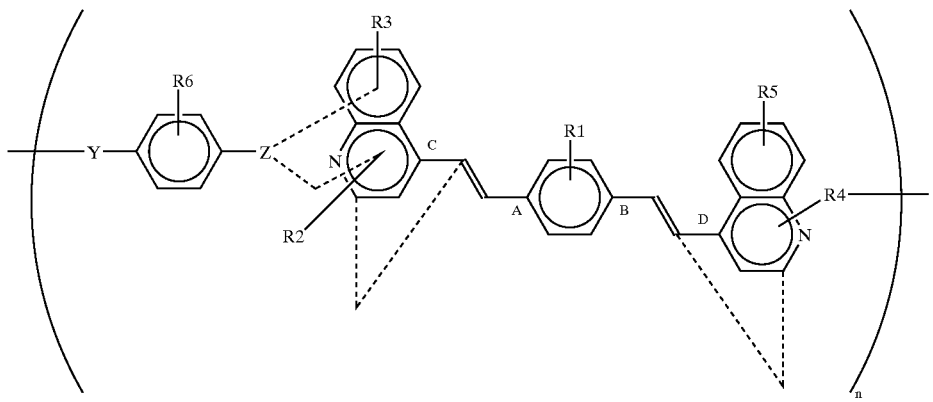

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; the R6 substituents are independently selected from the group consisting of hydrogen, alkyl groups, alkoxy groups, and aryl groups; wherein bonds A and B may independently be either ortho, meta or para from one another; wherein bond C may be either ortho, meta or para with respect to the respective quinoyl nitrogen; and wherein bond D may be either ortho, meta or para with respect to the respective quinoyl nitrogen; wherein Y may be a moiety attached at any point on ring R6, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; wherein Z may be a moiety bridging any two points on rings R2 or R3 and R6, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; and wherein n is an integer greater than 1.

These block co-polymers may have geometries and substituents, as do the oligomers from which they are derived, as described above.

Block Co-polymer of Oligomers 5, 6, 7 & 8 (Y Only)

The present invention also includes a composition of matter comprising a block co-polymer of the general structure:

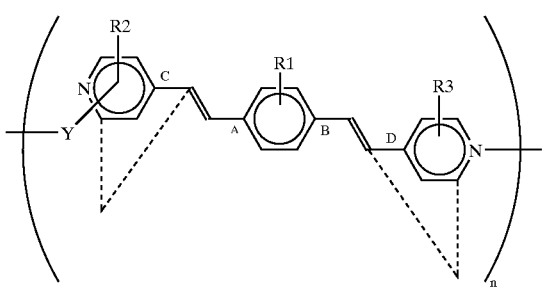

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; wherein bonds A and B may independently be either ortho, meta or para from one another; wherein bond C may be either ortho, meta or para with respect to the respective pyridyl nitrogen; wherein bond D may be either ortho, meta or para with respect to the respective pyridyl nitrogen; wherein Y may be a moiety attached at any point on ring R2, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; and wherein n is an integer greater than 1.

These block co-polymers may have geometries and substituents, as do the oligomers from which they are derived, as described above.

Block Co-polymer of Oligomers 5, 6, 7 & 8 (Y, R & Z)

The present invention also includes a composition of matter comprising a block co-polymer of the general structure:

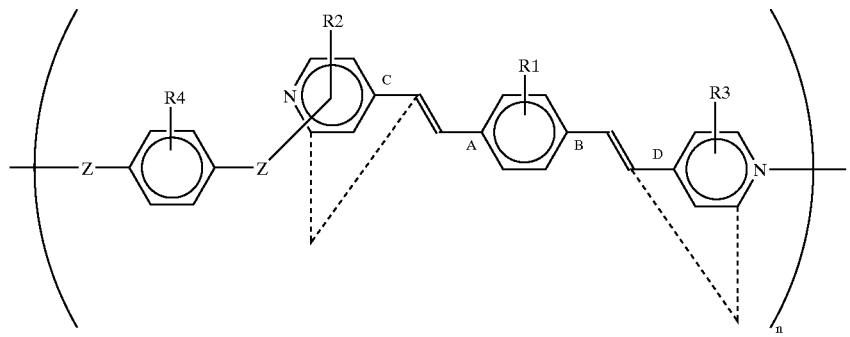

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; wherein bonds A and B may independently be either ortho, meta or para from one another; wherein bond C may be either ortho, meta or para with respect to the respective pyridyl nitrogen; wherein bond D may be either ortho, meta or para with respect to the respective pyridyl nitrogen; wherein Y may be a moiety attached at any point on ring R4, and may be selected from the group consisting of —$(CH_2)_x$—, —$(CH_2)_xO$—, —$O(CH_2)_x$— and —$O(CH_2)_x$O— wherein x is an integer in the range of 1 to 15 inclusive; wherein Z may be a moiety bridging any two points on rings R2 and R4, and may be selected from the group consisting of —$(CH_2)_x$—, —$(CH_2)_xO$—, —$O(CH_2)_x$— and —$O(CH_2)_x$O— wherein x is an integer in the range of 1 to 15 inclusive; and wherein n is an integer greater than 1.

These block co-polymers may have geometries and substituents as do the oligomers from which they are derived, as described above.

Block Co-polymer of Oligomers 9 & 10 (Y Only)

The present invention also includes a composition of matter comprising a block co-polymer of the general structure:

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; wherein bonds A and B may be either ortho, meta or para from one another; wherein Y may be a moiety attached at any point on rings R2 or R3, and may be selected from the group consisting of —$(CH_2)_x$—, —$(CH_2)_xO$—, —$O(CH_2)_x$— and —$O(CH_2)_xO$— wherein x is an integer in the range of 1 to 15 inclusive; and wherein n is an integer greater than 1.

These block co-polymers may have geometries and substituents as do the oligomers from which they are derived, as described above.

Block Co-polymer of Oligomers 9 & 10 (Y, R and Z Only)

The present invention also includes a composition of matter comprising a block co-polymer of the general structure:

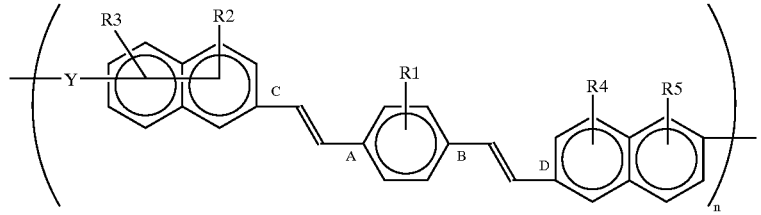

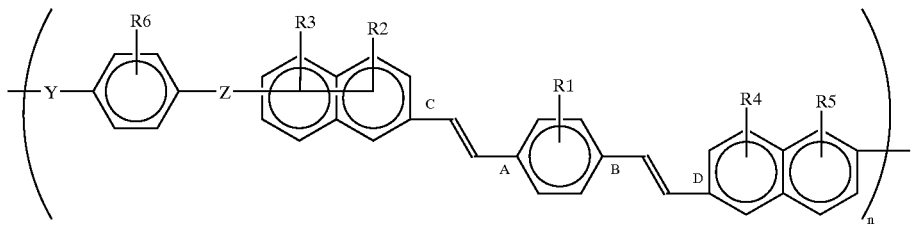

wherein the R1 substituents are independently selected from the group consisting of hydrogen, alkyl groups, alkoxy groups, and aryl groups; the R2 substituents are independently selected from the group consisting of hydrogen, alkyl groups, alkoxy groups, and aryl groups; the R3 substituents are independently selected from the group consisting of hydrogen, alkyl groups, alkoxy groups, and aryl groups; the R4 substituents are independently selected from the group consisting of hydrogen, alkyl groups, alkoxy groups, and aryl groups; the R5 substituents are independently selected from the group consisting of hydrogen, alkyl groups, alkoxy groups, and aryl groups; the R6 substituents are independently selected from the group consisting of hydrogen, alkyl groups, alkoxy groups, and aryl groups; wherein bonds A and B may be either ortho, meta or para from one another; wherein Y may be a moiety attached at any point on ring R6, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; wherein Z may be a moiety bridging any two points on rings R2 or R3 and R6, and may be selected from the group consisting of —(CH$_2$)$_x$—, —(CH$_2$)$_x$O—, —O(CH$_2$)$_x$— and —O(CH$_2$)$_x$O— wherein x is an integer in the range of 1 to 15 inclusive; and and wherein n is an integer greater than 1.

These block co-polymers may have geometries and substituents, as do the oligomers from which they are derived, as described above.

The compositions of the present invention may be used to fabricate a wide variety of electronic devices, such as those that may be made in accordance with known production procedures. These devices include polymeric light emitting devices, including mono- and multi-color devices, color-variable devices, infrared-emitting devices; so-called SCALE devices, including two-color and multi-color SCALE deveices. Other devices in which compositions of the present invention may be used include photovoltaic devices and polymer-based transistors. Examples of these devices that are disclosed in U.S. Pat. Nos. 6,004,681; 5,955,834; 5,858,561; 5,663,573 and several co-pending patent applications Ser. Nos. 09/041,337; 08/902,145; 08/901,888 and 60/187,278, all of which patents and patent applications are hereby incorporated herein by reference.

The compositions of the present invention may be ambipolar such that they may be used in layered polymeric devices, and may form part of as electron- or hole-transmissive materials and/or light emitting layers, in accordance with known arrangements. The compositions may also be used as components of blends in the devices described above.

DETAIL DESCRIPTION OF PREFERRED EMBODIMENT(S)

In accordance with the foregoing summary of the invention, the following represent illustrative examples of the invention, and include the best mode. The preferred embodiments herein described are not intended to be exhaustive or to limit the invention to the precise variations disclosed. They are chosen and described to explain the compositions and methods of the invention, and the application of the compositions, so that others skilled in the art may practice the invention.

The following describe a procedure for making the monomers from which the Polymers 1 & 2 (described in Examples 1 & 2) may be produced.

Monomer Synthesis

Following are the monomer synthetic scheme of Polymer 1 and Polymer 2:

Monomer (1) in Polymer 1:

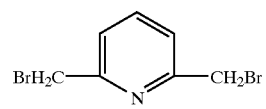
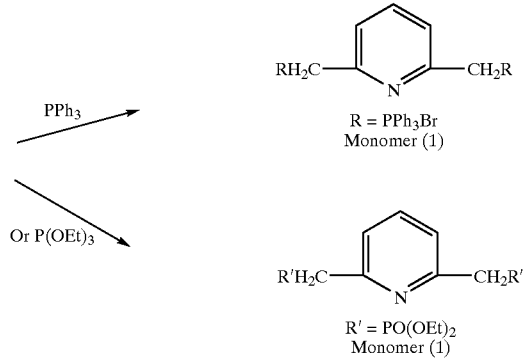

(Similar synthetic method can be found from Macromolecule, 26, 1188–1190, 1993)

Monomer (2) in Polymer 1:

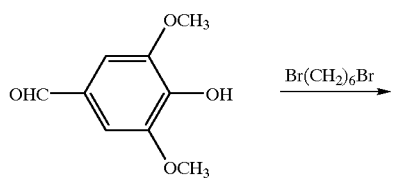

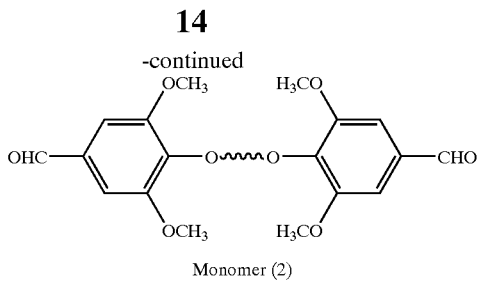

Monomer (2)

(Similar synthetic method can be found from the Macromolecule, 26, 1188–1190, 1993)
Monomer (1)+Monomer (2)→Polymer 1

EXAMPLE 1

Polymer 1: 150 mg

This Example shows the synthetic scheme through which a polymer in accordance with one embodiment of the present invention may be produced.

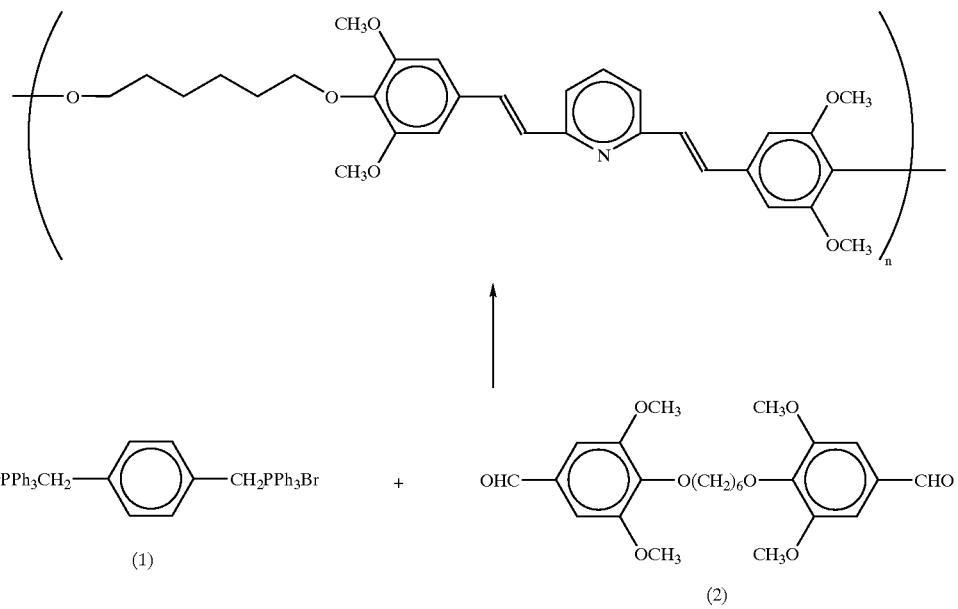

To a stirred solution of 502 mg (1.12 mmol) of the dialdehyde (2) and 890 mg (1.12 mmol) of the 1,4-pyridylylenebis(triphenylphosphonium) (1) in 150 ml THF was added dropwise a solution of 10 ml KotBu (2M in THF) (excess). The mixture was refluxed for 2 h after the addition. Remove the THF and the solid product was dissolved in $CHCl_3$, and then precipitate from MeOH. The resulting precipitate was collected by suction filtration. Further purification by Soxhlet extraction with methanol for 12 hours afforded Polymer 1 as a light-yellow solid. The solid product was dried in a vacuum oven at 50° C. for 2 days (92% yield). The following NMR data was obtained: $^1$H-NMR($CDCl_3$): 1.4 (m, 4H), 1.6 (t, 4H), 3.7 (s, 12H), 3.9 (t, 4H), 6.7 (s, 4H), 7.0 (t, 1H), 7.1 (d, 4H), 7.5 (d, 2H).

EXAMPLE 2

Polymer 2: 360 mg

This Example shows the synthetic scheme through which a polymer in accordance with another embodiment of the present invention may be produced.

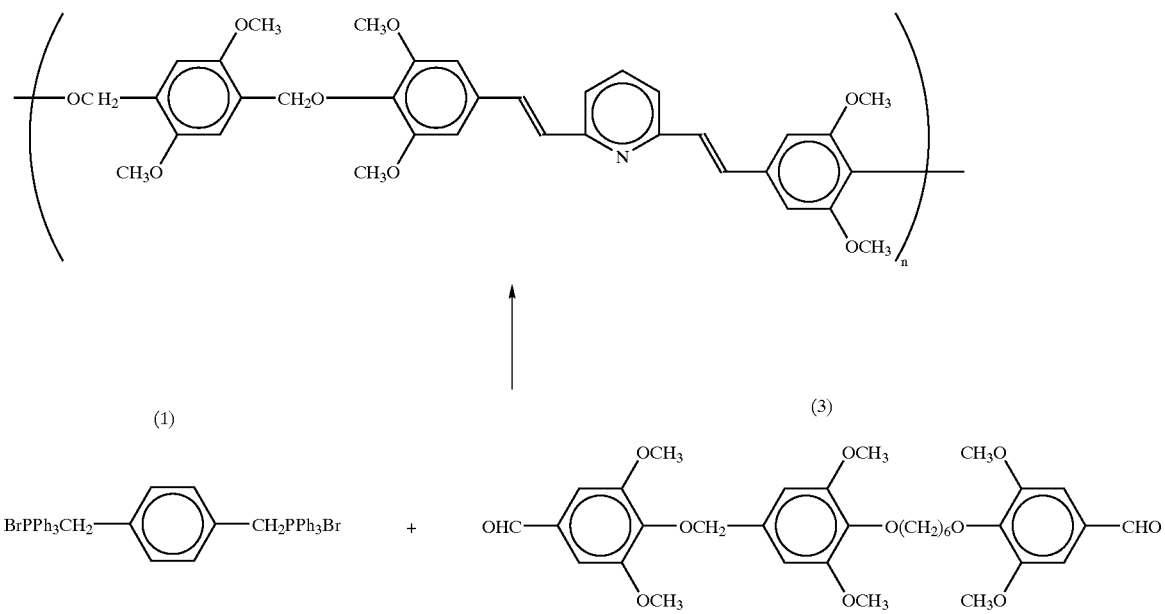

To a stirred solution of 1.2 g (2.28 mmol) of the dialdehyde (3) and 1.8 g (2.28 mmol) of the 1,4-pyridylylenebis(triphenylphosphonium) (1) in 150 ml THF was added dropwise a solution of 10 ml KotBu (2M in THF) (excess). The mixture was refluxed for 2 h after the addition. Remove the THF and the solid product was dissolved in $CHCl_3$, and then precipitate from MEOH. The resulting precipitate was collected by suction filtration. Further purification by Soxhlet extraction with methanol for 12 hours afforded Polymer 2 as a light-yellow solid. The solid product was dried in a vacuum oven at 50° C. for 2 days (90% yield). The following NMR data was obtained: $^1$H-NMR($CDCl_3$): 3.7 (d, 18H), 5.0 (s, 4H), 6.7 (s, 4H), 6.8, (s, 2H), 7.0 (t, 1H), 7.1 (d, 4H), 7.5 (d, 2H).

EXAMPLE 3

Oligomer 1: 116 mg

This Example shows the synthetic scheme through which an oligomer in accordance with another embodiment of the present invention may be produced.

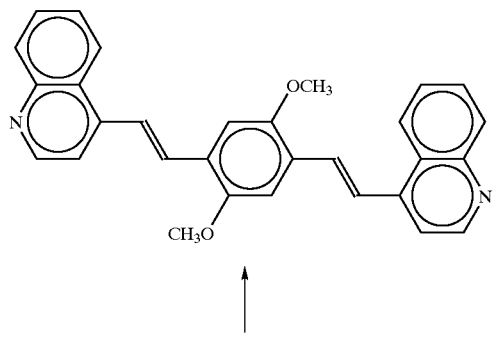

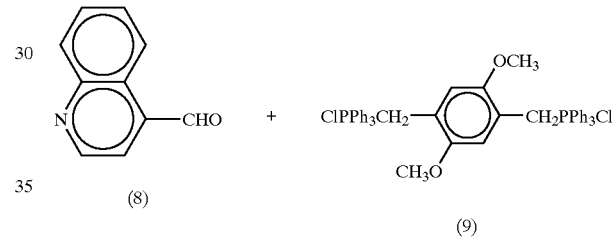

To a stirred solution of 0.91 g (5.80 mmol) of the 4-quinolinecarboxaldehyde (8) and 2.0 g (2.63 mmol) of the [2,5-dimethoxy-1,4-xylylene]-bis(triphenylphosphonium chloride) (9) in 50 ml ethanol was added dropwise a solution of 10 ml EtONa (2M in ethanol) (excess). The mixture was stirred for 2 h after the addition. Remove the ethanol and the solid product was washed with hexane and water. Dissolve the product with ethyl acetate followed by flash column chromatography (SiO2, Hexane:ethyl acetate=1:1) gave the desired product as an orange solid. The solid product was then recrystallized from hexane and ethyl acetate to give an orange crystal (yield=55%). The following NMR data was obtained: $^1$H-NMR($CDCl_3$): 4.0 (s, 6H), 7.2 (d, 4H), 7.7 (m, 6H), 7.9 (d, 2H), 8.1 (d, 2H), 8.2 (d, 2H), 8.9 (d, 2H).

EXAMPLE 4

Oligomer 2: 60 mg

This Example shows the synthetic scheme through which an oligomer in accordance with another embodiment of the present invention may be produced.

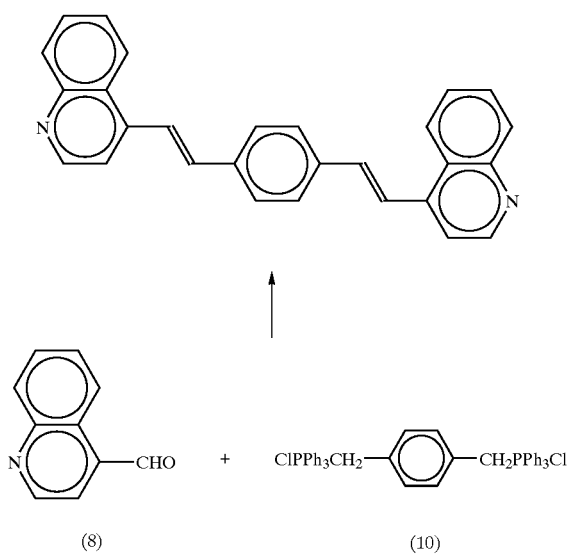

To a stirred solution of 0.32 g (2.04 mmol) of the 4-quinolinecarboxaldehyde (8) and 0.85 g (1.21 mmol) of the 1,4-xylylene-bis(triphenylphosphonium chloride) (10) in 500 ml ethanol was added dropwise a solution of 10 ml EtONa (2M in ethanol) (excess). The mixture was stirred for 2 h after the addition. Remove the ethanol and the solid product was washed with hexane and water. Dissolve the product with ethyl acetate followed by flash column chromatography (SiO2, Hexane:ethyl acetate=1:1) gave the desired product as a yellow solid. The solid product was then recrystallized from hexane and ethyl acetate to give a light-yellow crystal (yield=59%). The following NMR data was obtained: $^1$H-NMR(CDCl$_3$): 7.2 (d, 2H), 7.4 (d, 2H), 7.7 (m, 8H), 7.9 (d, 2H), 8.1 (d, 2H), 8.2 (d, 2H), 8.9 (d, 2H).

EXAMPLE 5

Oligomer 3: 30 mg

This Example shows the synthetic scheme through which an oligomer in accordance with another embodiment of the present invention may be produced.

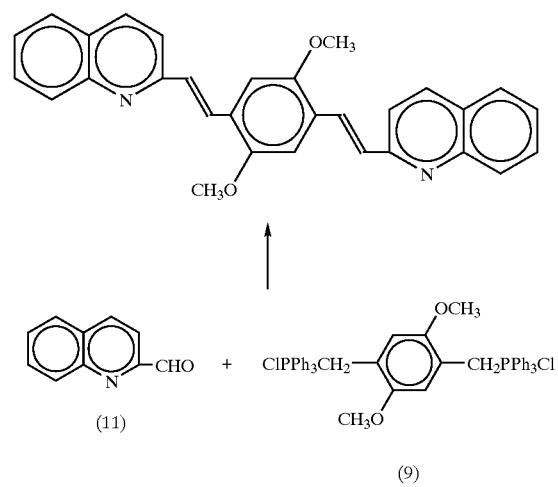

To a stirred solution of 1.0 g (6.37 mmol) of the 2-quinolinecarboxaldehyde (11) and 2.2 g (2.90 mmol) of the [2,5-dimethoxy-1,4-xylylene]-bis(triphenylphosphonium chloride) (9) in 150 ml ethanol was added dropwise a solution of 10 ml EtONa (2M in ethanol) (excess). The mixture was stirred for 2 h after the addition. Remove the ethanol and the solid product was washed with hexane and water. Dissolve the product with chloroform followed by flash column chromatography (SiO2, Hexane:ethyl acetate=1:1) gave the desired product as an orange-yellow solid. The solid product was then recrystallized from hexane and ethyl acetate to give an orange-yellow crystal (yield=49%). The following NMR data was obtained: $^1$H-NMR(CDCl$_3$): 4.0 (s, 6H), 7.3 (d, 4H), 7.5 (m, 4H), 8.0 (m, 6H), 8.1 (m, 4H).

EXAMPLE 6

Oligomer 4: 100 mg

This Example shows the synthetic scheme through which an oligomer in accordance with another embodiment of the present invention may be produced.

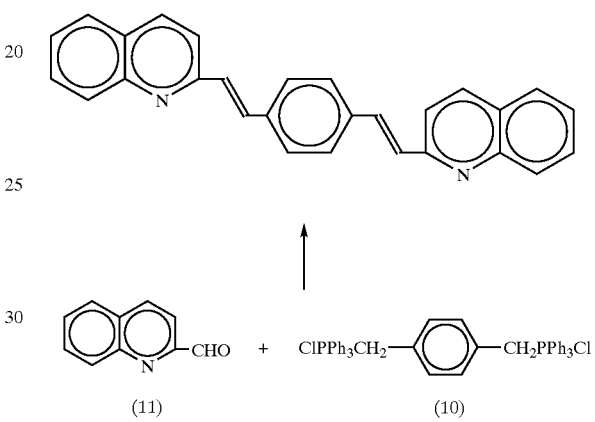

To a stirred solution of 3.2 g (20.38 mmol) of the 2-quinolinecarboxaldehyde (11) and 8.5 g (12.14 mmol) of the 1,4-xylylene-bis(triphenylphosphonium chloride) (10) in 100 ml ethanol was added dropwise a solution of 30 ml EtONa (2M in ethanol) (excess). The mixture was stirred for 2 h after the addition. Remove the ethanol and the solid product was washed with hexane and water. Dissolve the product with chloroform followed by flash column chromatography (SiO2, Hexane:ethyl acetate=1:1) gave the desired product as a light-yellow solid. The solid product was then recrystallized from hexane and ethyl acetate to give a light-yellow crystal (yield=48%). The following NMR data was obtained: $^1$H-NMR(CDCl$_3$): 7.1 (d, 2H), 7.3 (d, 2H), 7.4 (m, 4H), 7.7 (m, 8H), 8.0 (m, 4H)

EXAMPLE 7

Oligomer 5: 10 mg

This Example shows the synthetic scheme through which an oligomer in accordance with another embodiment of the present invention may be produced.

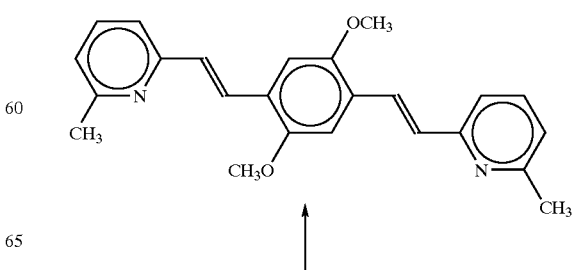

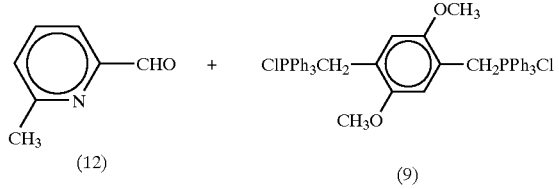

(12)　　　　　(9)

To a stirred solution of 0.16 g (1.32 mmol) of the 6-methyl-2-pyridinecarboxaldehyde (12) and 0.5 g (0.66 mmol) of the [2,5-dimethoxy-1,4-xylylene]-bis(triphenylphosphonium chloride) (9) in 50 ml ethanol was added dropwise a solution of 10 ml EtONa (2M in ethanol) (excess). The mixture was stirred overnight after the addition. Remove the ethanol and the solid product was washed with hexane and water. Dissolve the product with ethyl acetate followed by flash column chromatography (SiO2, Hexane:ethyl acetate=1:1) gave the desired product as a green solid. The solid product was then recrystallized from hexane and ethyl acetate to give a green crystal (yield=57%). The following NMR data was obtained: $^1$H-NMR(CDCl$_3$): 2.5 (s, 6H), 3.8 (s, 6H), 6.9 (d, 2H), 7.1 (d, 4H), 7.4 (t, 2H), 7.5 (s, 2H), 7.7 (d, 2H).

EXAMPLE 8

Oligomer 6: 20 mg

This Example shows the synthetic scheme through which an oligomer in accordance with another embodiment of the present invention may be produced.

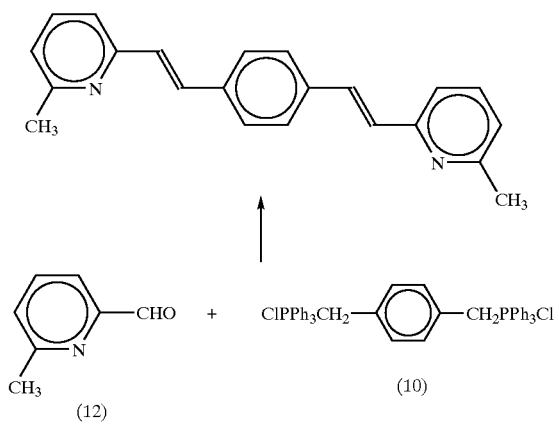

(12)　　　　　(10)

To a stirred solution of 0.17 g (1.40 mmol) of the 6-methyl-2-pyridinecarboxaldehyde (12) and 0.5 g (0.71 mmol) of the 1,4-xylylene-bis(triphenylphosphonium chloride) (10) in 50 ml ethanol was added dropwise a solution of 10 ml EtONa (2M in ethanol) (excess). The mixture was stirred overnight after the addition. Remove the ethanol and the solid product was washed with hexane and water. Dissolve the product with chloroform followed by flash column chromatography (SiO2, Hexane:ethyl acetate=1:1) gave the desired product as light-yellow solid. The solid product was then recrystallized from hexane and ethyl acetate to give a light-yellow crystal (yield=52%). The following NMR data was obtained: $^1$H-NMR(CDCl$_3$): 2.5 (s, 6H), 6.7 (d, 4H), 7.1 (d, 4H), 7.4 (t, 2H), 7.5 (d, 2H), 7.7 (d, 2H).

EXAMPLE 9

Oligomer 7: 40 mg

This Example shows the synthetic scheme through which an oligomer in accordance with another embodiment of the present invention may be produced.

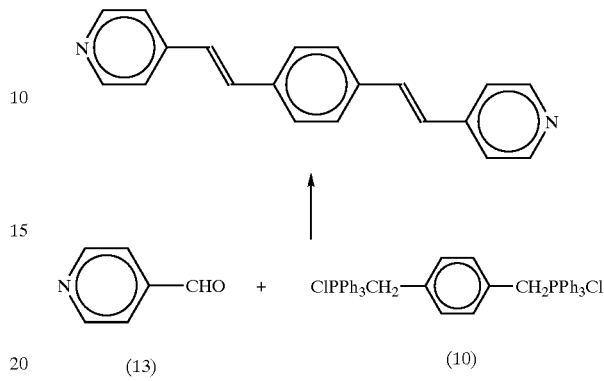

(13)　　　　　(10)

To a stirred solution of 0.38 g (3.55 mmol) of the 4-pyridinecarboxaldehyde (13) and 1.0 g (1.43 mmol) of the 1,4-xylylene-bis(triphenylphosphonium chloride) (10) in 50 ml ethanol was added dropwise a solution of 10 ml EtONa (2M in ethanol) (excess). The mixture was stirred for 3 h after the addition. Remove the ethanol and the solid product was washed with hexane and water. Dissolve the product with chloroform followed by flash column chromatography (SiO2, Hexane:ethyl acetate=1:1) gave the desired product as light-yellow solid. The solid product was then recrystallized from hexane and ethyl acetate to give a light-yellow crystal (yield=43%). The following NMR data was obtained: $^1$H-NMR(CDCl$_3$): 7.0 (d, 4H), 7.3 (d, 4H), 7.5 (d, 4H), 8.4 (d, 4H).

EXAMPLE 10

Oligomer 8: 30 mg

This Example shows the synthetic scheme through which an oligomer in accordance with another embodiment of the present invention may be produced.

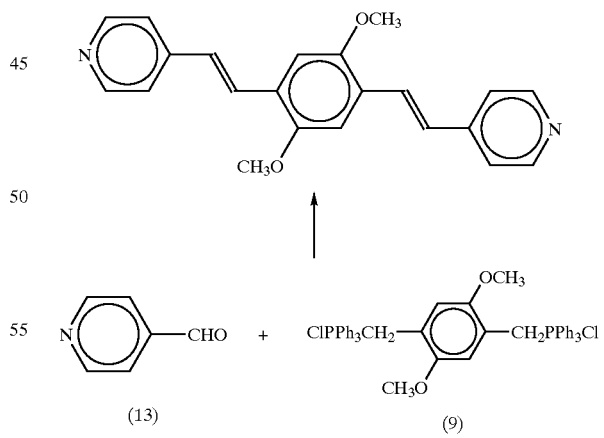

(13)　　　　　(9)

To a stirred solution of 0.38 g (3.55 mmol) of the 4-pyridinecarboxaldehyde (13) and 1.0 g (1.32 mmol) of the [2,5-dimethoxy-1,4-xylylene]-bis(triphenylphosphonium chloride) (9) in 50 ml ethanol was added dropwise a solution of 10 ml EtONa (2M in ethanol) (excess). The mixture was stirred for 3 h after the addition. Remove the ethanol and the solid product was washed with hexane and water. Dissolve the product with chloroform followed by flash column chromatography (SiO2, Hexane:ethyl acetate=1:1) gave the desired product as orange solid. The solid product was then recrystallized from hexane and ethyl acetate to give an orange crystal (yield=46%). The following NMR data was obtained: $^1$H-NMR(CDCl$_3$): 3.8 (s, 6H), 7.0 (d, 4H), 7.3 (d, 4H), 7.5 (s, 2H), 8.5 (d, 4H).

EXAMPLE 11

Oligomer 9: 320 mg

This Example shows the synthetic scheme through which an oligomer in accordance with another embodiment of the present invention may be produced.

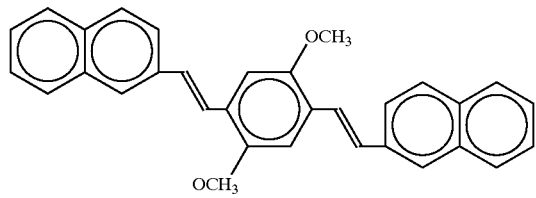

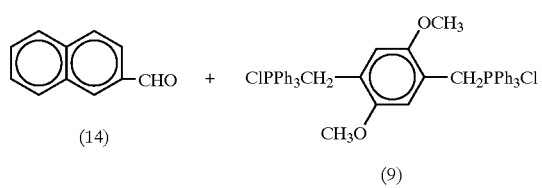

To a stirred solution of 0.24 g (0.15 mmol) of the 2-naphthaldehyde (14) and 0.5 g (0.071 mmol) of the [2,5-dimethoxy-1,4-xylylene]-bis(triphenylphosphonium chloride) (9) in 50 ml ethanol was added dropwise a solution of 10 ml EtONa (2M in ethanol) (excess). The mixture was stirred for 3 h after the addition. Remove the ethanol and the solid product was washed with hexane and water. Dissolve the product with chloroform followed by flash column chromatography (SiO2, Hexane:ethyl acetate=1:1) gave the desired product as green solid. The solid product was then recrystallized from hexane and ethyl acetate to give a green crystal (yield=59%). The following NMR data was obtained: $^1$H-NMR(CDCl$_3$): 3.8 (s, 6H), 6.7 (s, 2H), 7.1 (d, 4H), 7.3 (m, 4H), 7.6 (m, 8H).

EXAMPLE 12

Oligomer 10: 400 mg

This Example shows the synthetic scheme through which an oligomer in accordance with another embodiment of the present invention may be produced.

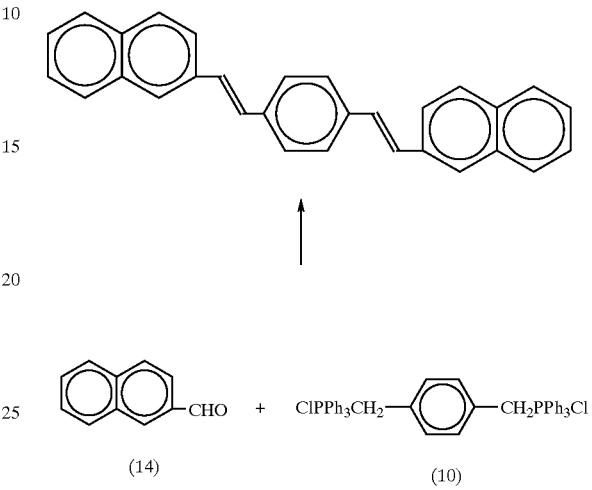

To a stirred solution of 0.24 g (0.15 mmol) of the 2-naphthaldehyde (14) and 0.5 g (0.071 mmol) of the [2,5-dimethoxy-1,4-xylylene]-bis(triphenylphosphonium chloride) (9) in 50 ml ethanol was added dropwise a solution of 10 ml EtONa (2M in ethanol) (excess). The mixture was stirred for 3 h after the addition. Remove the ethanol and the solid product was washed with hexane and water. Dissolve the product with chloroform followed by flash column chromatography (SiO2, Hexane:chloroform=1:1) gave the desired product as light-yellow solid (yield=50%). The following NMR data was obtained: $^1$H-NMR(CDCl$_3$): 3.8 (s, 6H), 6.7 (s, 2H), 7.1 (d, 4H), 7.3 (m, 8H), 7.6 (m, 8H).

EXAMPLE 13

Polymer 6

This Example shows the synthetic scheme through which a polymer in accordance with another embodiment of the present invention may be produced.

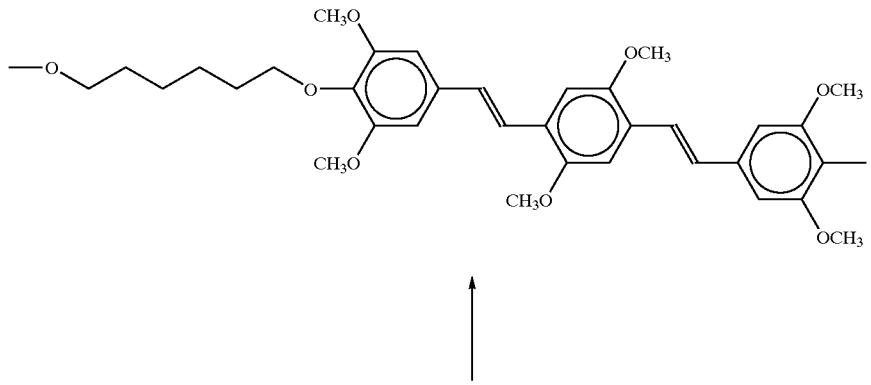

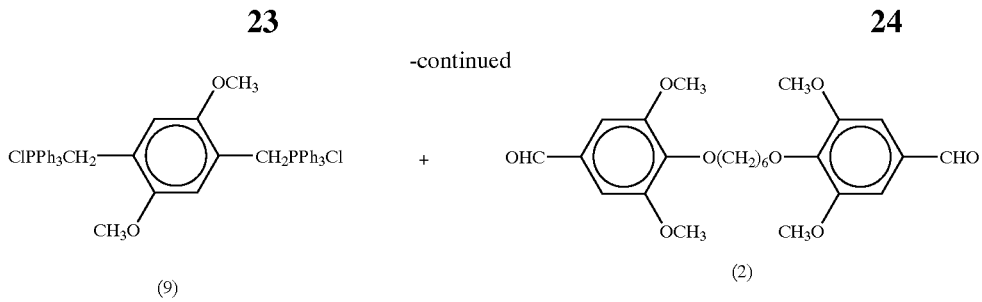

To a stirred solution of 600 mg (1.34 mmol) of the dialdehyde (2) and 1.02 g (1.34 mmol) of the [2,5-dimethoxy-1,4-xylylene]-bis(triphenylphosphonium chloride) (9) in 100 ml $CHCl_3$/EtOH (1:3) was added dropwise a solution of 10 ml EtONa (2M in ethanol) (excess). The mixture was refluxed overnight after the addition. Remove the solvents and the solid product was washed with dilute HCl, and then dissolved in $CHCl_3$, and then precipitate from ethanol. The resulting precipitate was collected by suction filtration. Further purification by Soxhlet extraction with methanol for 24 hours afforded Polymer 6 as a green solid. The solid product was dried in a vacuum oven at 50° C. for 2 days (88% yield). The following NMR data was obtained: $^1$H-NMR(CDCl$_3$): 1.4 (m, 4H), 1.6 (m, 4H), 3.7 (s, 12H), 3.9 (t, 4H), 4,1 (s, 6H), 6.7 (s, 4H), 7.1 (d, 4H), 7.5 (d, 2H).

EXAMPLE 14

Polymer 7: 60 mg

This Example shows the synthetic scheme through which a polymer in accordance with another embodiment of the present invention may be produced.

refluxed overnight after the addition. Remove the solvents and the solid product was washed with dilute HCl, and then dissolved in $CHCl_3$, and then precipitate from ethanol. The resulting precipitate was collected by suction filtration. Further purification by Soxhlet extraction with methanol for 24 hours afforded Polymer 7 as a green solid. The solid product was dried in a vacuum oven at 50° C. for 2 days (90% yield). The following NMR data was obtained: $^1$H-NMR(CDCl$_3$): 1.4 (m, 4H), 1.6 (m, 4H), 3.7 (s, 6H), 3.9 (t, 4H), 4,1 (s, 6H), 6.7 (s, 2H), 7.1 (d, 4H), 7.5 (m, 6H).

EXAMPLE 15

Polymer 8: 70 mg

This Example shows the synthetic scheme through which a polymer in accordance with another embodiment of the present invention may be produced.

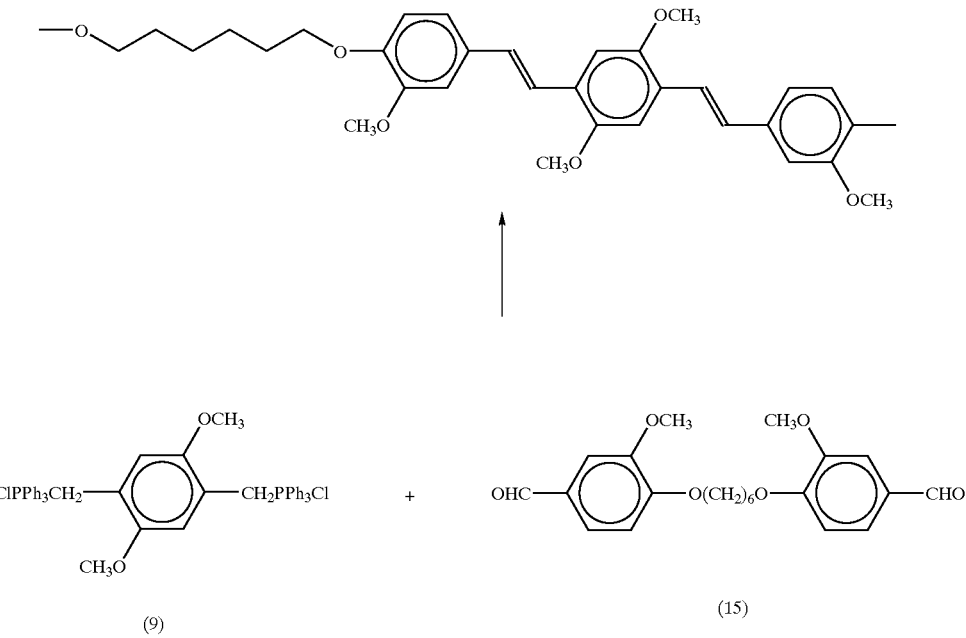

To a stirred solution of 1.0 g (2.59 mmol) of the dialdehyde (15) and 1.97 g (2.59 mmol) of the [2,5-dimethoxy-1,4-xylylene]-bis(triphenylphosphonium chloride) (9) in 100 ml $CHCl_3$/EtOH (1:3) was added dropwise a solution of 10 ml EtONa (2M in ethanol) (excess). The mixture was

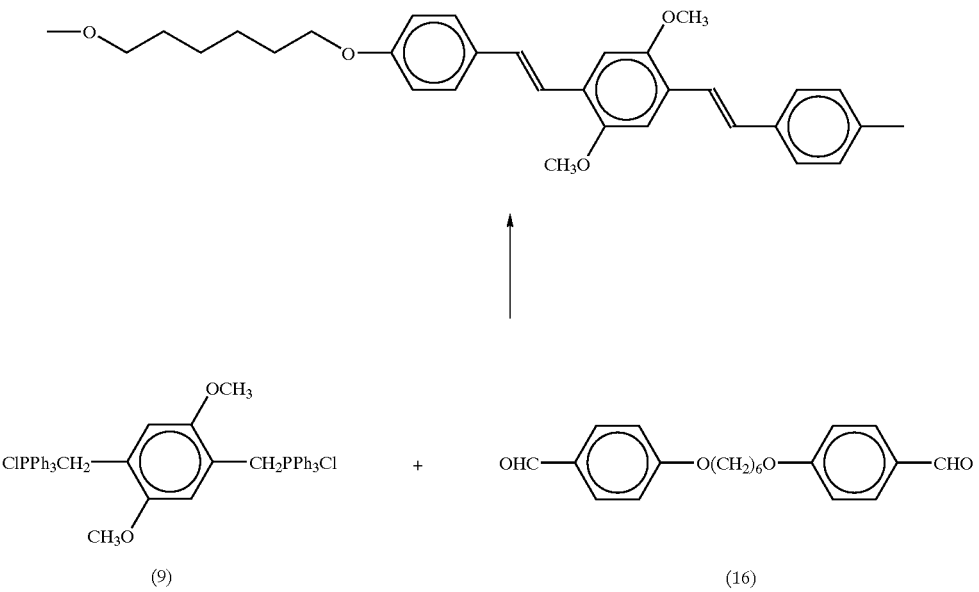

(9)	(16)

EXAMPLE 16

Polymer 9: 110 mg

This Example shows the synthetic scheme through which a polymer in accordance with another embodiment of the present invention may be produced.

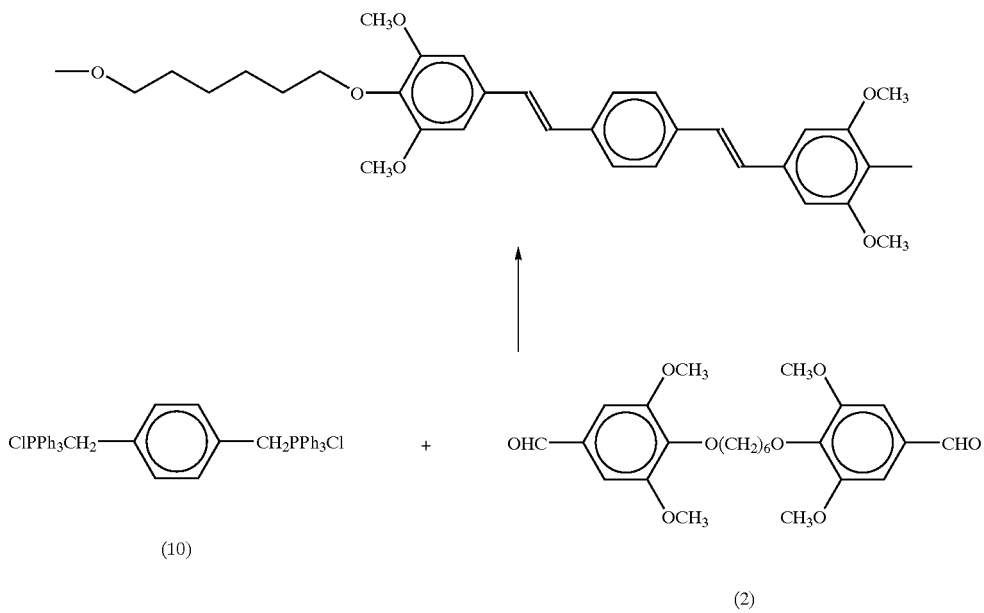

(10)	(2)

To a stirred solution of 1.0 g (3.07 mmol) of the dialdehyde (16) and 2.33 g (3.07 mmol) of the [2,5-dimethoxy-1,4-xylylene]-bis(triphenylphosphonium chloride) (9) in 100 ml $CHCl_3$/EtOH (1:3) was added dropwise a solution of 10 ml EtONa (2M in ethanol) (excess). The mixture was refluxed overnight after the addition. Remove the solvents and the solid product was washed with dilute HCl, and then dissolved in $CHCl_3$, and then precipitate from ethanol. The resulting precipitate was collected by suction filtration. Further purification by Soxhlet extraction with methanol for 24 hours afforded Polymer 8 as a green solid. The solid product was dried in a vacuum oven at 50° C. for 2 days (90% yield). The following NMR data was obtained: $^1$H-NMR($CDCl_3$): 1.4 (m, 4H), 1.6 (m, 4H), 3.7 (s, 6H), 3.9 (t, 4H), 4,1 (s, 6H), 6.7 (s, 2H), 7.1 (d, 4H), 7.5 (m, 8H).

To a stirred solution of 2.0 mg (4.48 mmol) of the dialdehyde (2) and 3.14 g (4.48 mmol) of the 1,4-xylylene-bis(triphenylphosphonium chloride) (10) in 100 ml $CHCl_3$/EtOH (1:3) was added dropwise a solution of 10 ml EtONa (2M in ethanol) (excess). The mixture was refluxed overnight after the addition. Remove the solvents and the solid product was washed with dilute HCl, and then dissolved in CHCl₃, and then precipitate from ethanol. The resulting precipitate was collected by suction filtration. Further purification by Soxhlet extraction with methanol for 24 hours afforded Polymer 9 as almost light-yellow solid. The solid product was dried in a vacuum oven at 50° C. for 2 days (88% yield). The following NMR data was obtained: ¹H-NMR(CDCl₃): 1.4 (m, 4H), 1.6 (m, 4H), 3.7 (s, 12H), 3.9 (t, 4H), 6.7 (s, 4H), 7.1 (d, 4H), 7.5 (d, 4H).

EXAMPLE 17

Oligomer 11: 300 mg

This Example shows the synthetic scheme through which an oligomer in accordance with another embodiment of the present invention may be produced.

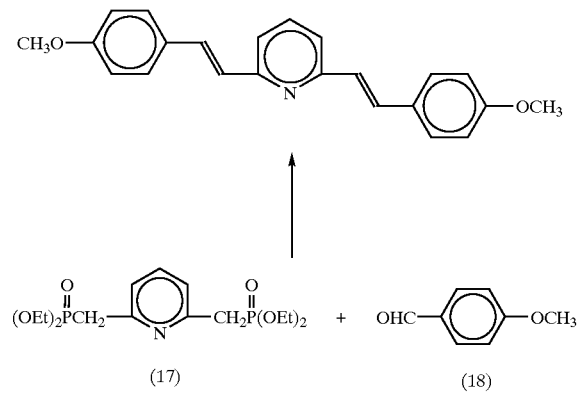

To a stirred solution of 1.2 g (10 mmol) of the p-anisaldehyde (18) and 1.32 g (4.0 mmol) of the monomer (17) in 50 ml THF was added dropwise a solution of 10 ml KOtBu (2M in THF) (excess). The mixture was stirred for 1 h after the addition. Remove the THF and the solid product was washed with hexane and water. Dissolve the product with chloroform followed by flash column chromatography (SiO2, Hexane:ethyl acetate=1:1) gave the desired product as light-yellow solid. The solid product was then recrystallized from hexane and ethyl acetate to give a colorless crystal (yield=45%). The following NMR data was obtained: ¹H-NMR(CDCl₃): 3.7 (s, 6H), 6.8 (d, 4H), 7.0 (d, 4H), 7.1 (d, 4H), 7.5 (m, 3H).

EXAMPLE 18

Oligomer 12: 100 mg

This Example shows the synthetic scheme through which an oligomer in accordance with another embodiment of the present invention may be produced.

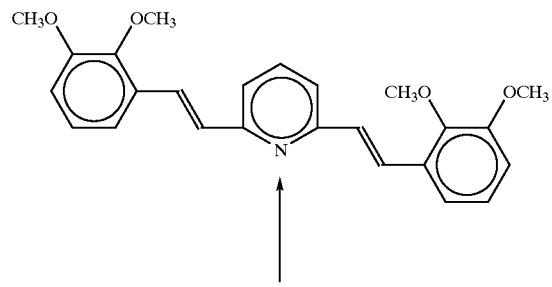

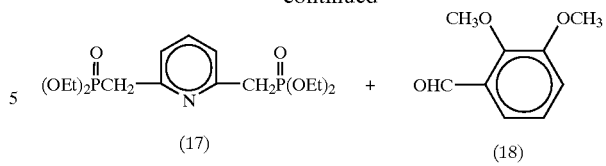

To a stirred solution of 1.0 g (9.64 mmol) of the 2,3-dimethoxybenzaldehyde (19) and 1.38 g (4.19 mmol) of the monomer (17) in 50 ml THF was added dropwise a solution of 10 ml KOtBu (2M in THF) (excess). The mixture was stirred for 1 h after the addition. Remove the THF and the solid product was washed with hexane and water. Dissolve the product with chloroform followed by flash column chromatography (SiO2, Hexane:ethyl acetate=1:1) gave the desired product as white solid. The solid product was then recrystallized from hexane and ethyl acetate to give a colorless crystal (yield=56%). The following NMR data was obtained: ¹H-NMR(CDCl₃): 3.8 (d, 12H), 6.7 (d, 2H), 6.9 (t, 2H), 7.1 (d, 4H), 7.2 (d, 4H), 7.5 (t, 1H), 7.9 (d, 2H).

EXAMPLE 19

Oligomer 13: 100 mg

This Example shows the synthetic scheme through which an oligomer in accordance with another embodiment of the present invention may be produced.

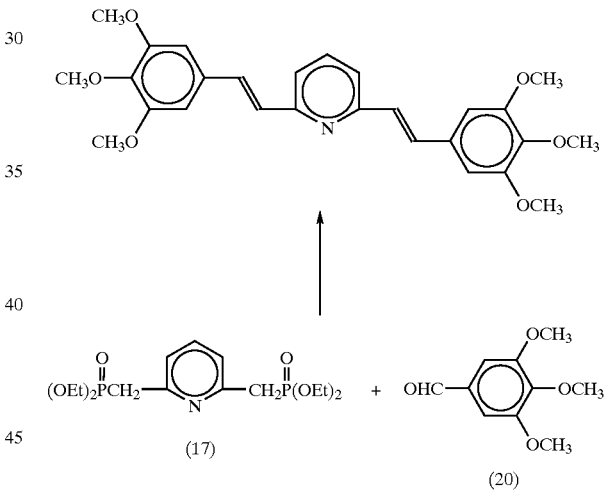

To a stirred solution of 0.17 g (0.87 mmol) of the 2,3,4-trimethoxybenzaldehyde (20) and 0.12 g (0.35 mmol) of the monomer (17) in 50 ml THF was added dropwise a solution of 10 ml KOtBu (2M in THF) (excess). The mixture was stirred for 1 h after the addition. Remove the THF and the solid product was washed with hexane and water. Dissolve the product with chloroform followed by flash column chromatography (SiO2, Hexane:ethyl acetate=1:1) gave the desired product as white solid. The solid product was then recrystallized from hexane and ethyl acetate to give a light-yellow crystal (yield=53%). The following NMR data was obtained: ¹H-NMR(CDCl₃): 3.8 (d, 18H), 6.7 (s, 4H), 7.0 (d, 2H), 7.2 (d, 2H), 7.5 (m, 3H).

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A composition of matter comprising a polymer of the general structure:

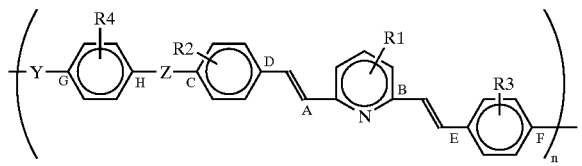

wherein the R1 substituents are independently selected from the group consisting of hydrogen, alkyl groups, alkoxy groups, and aryl groups;

the R2 substituents are independently selected from the group consisting of hydrogen, alkyl groups, alkoxy groups, and aryl groups;

the R3 substituents are independently selected from the group consisting of hydrogen, alkyl groups, alkoxy groups, and aryl groups;

the R4 substituents are independently selected from the group consisting of hydrogen, alkyl groups, alkoxy groups, and aryl groups;

wherein bonds A and B may be either ortho or para with respect to the pyridyl nitrogen;

wherein bonds C and D may independently be either ortho, meta or para with respect one another;

wherein bonds E and F may be either ortho, meta or para with respect one another;

wherein bonds G and H may be either ortho, meta or para with respect one another;

wherein Y may be a moiety selected from the group consisting of —$(CH_2)_x$—, —$(CH_2)_xO$—, —$O(CH_2)_x$— and —$O(CH_2)_xO$— wherein x is an integer in the range of 1 to 15 inclusive;

wherein Z may be a moiety selected from the group consisting of —$(CH_2)_x$—, —$(CH_2)_xO$—, —$O(CH_2)_x$— and —$O(CH_2)_xO$— wherein x is an integer in the range of 1 to 15 inclusive; and wherein n is an integer greater than 1.

2. A composition according to claim 1 wherein at least one R2 substituent is a methoxy group.

3. A composition according to claim 1 wherein at least two R2 substituents are methoxy groups.

4. A composition according to claim 1 wherein at least one R3 substituent is a methoxy group.

5. A composition according to claim 1 wherein at least two R3 substituents are methoxy groups.

6. A composition according to claim 1 wherein at least one R3 substituent is a methoxy group.

7. A composition according to claim 1 wherein at least two R3 substituents are methoxy groups.

8. A composition according to claim 1 wherein vinyl linkage A attaches at a position ortho to the pyridyl nitrogen.

9. A composition according to claim 1 wherein vinyl linkage B attaches at a position ortho to the pyridyl nitrogen.

10. A composition according to claim 1 wherein vinyl linkage A attaches at a position para to the pyridyl nitrogen.

11. A composition according to claim 1 wherein vinyl linkage B attaches at a position para to the pyridyl nitrogen.

12. A composition according to claim 1 wherein x is an integer in the range of 1 to 6 inclusive.

* * * * *

UNITED STATES PATENT AND TRADEMARK OFFICE
CERTIFICATE OF CORRECTION

PATENT NO.        : 6,906,166 B2                                        Page 1 of 3
APPLICATION NO. : 10/847896
DATED             : June 14, 2005
INVENTOR(S)      : Epstein et al.

It is certified that error appears in the above-identified patent and that said Letters Patent is hereby corrected as shown below:

In columns 13-14, lines 20-40, please delete

"
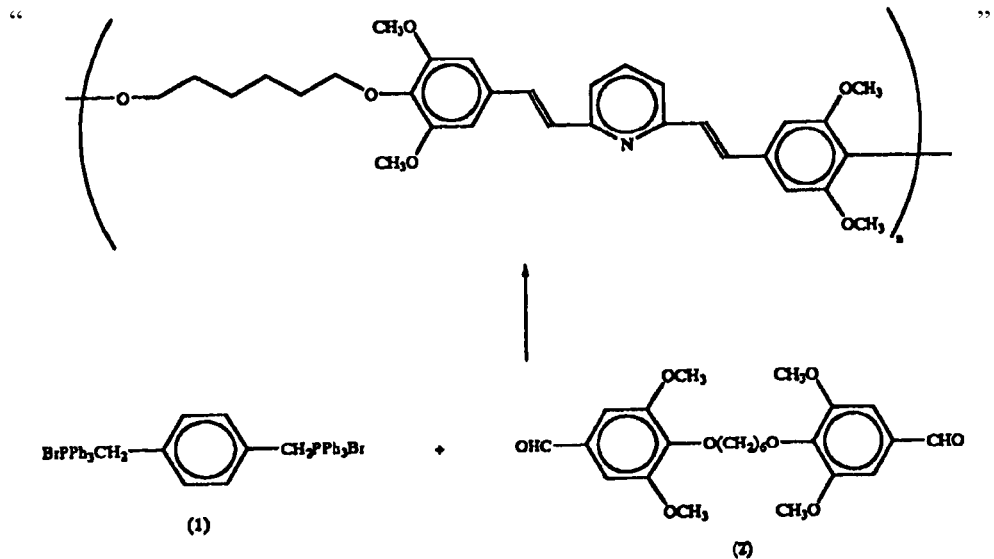
"

and insert

--
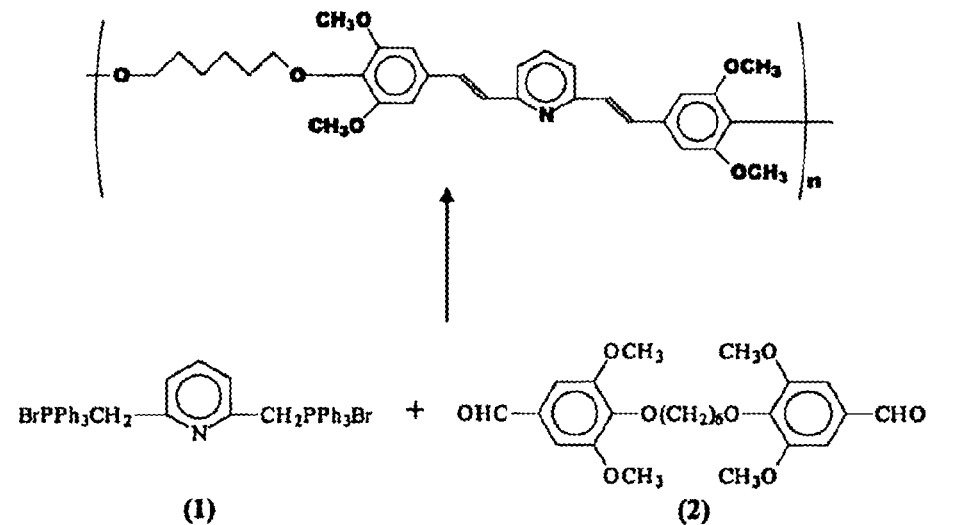
--.

UNITED STATES PATENT AND TRADEMARK OFFICE
CERTIFICATE OF CORRECTION

PATENT NO.       : 6,906,166 B2
APPLICATION NO.  : 10/847896
DATED            : June 14, 2005
INVENTOR(S)      : Epstein et al.

It is certified that error appears in the above-identified patent and that said Letters Patent is hereby corrected as shown below:

In columns 15-16, lines 1-25, please delete

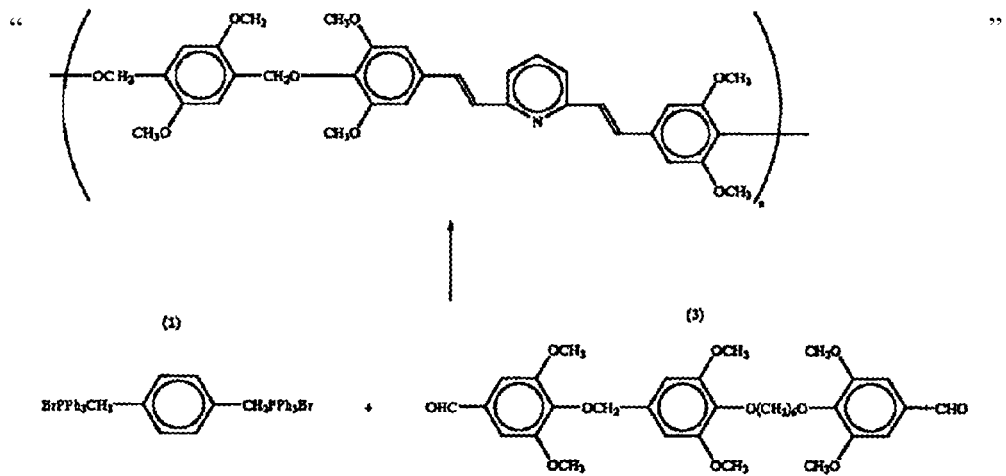

and insert

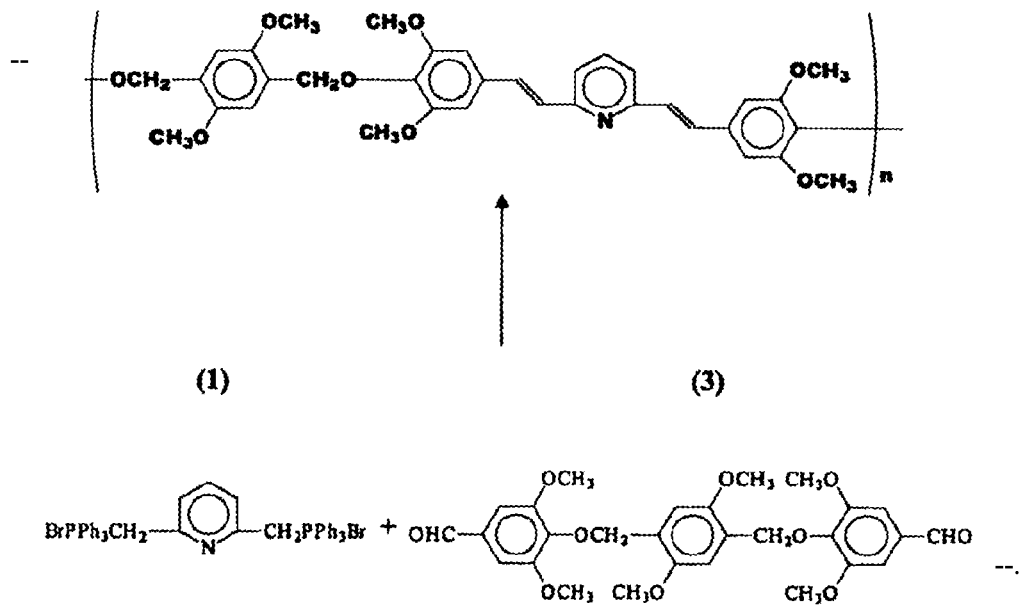

UNITED STATES PATENT AND TRADEMARK OFFICE
CERTIFICATE OF CORRECTION

PATENT NO. : 6,906,166 B2
APPLICATION NO. : 10/847896
DATED : June 14, 2005
INVENTOR(S) : Epstein et al.

Page 3 of 3

It is certified that error appears in the above-identified patent and that said Letters Patent is hereby corrected as shown below:

In column 28, lines 1-8, please delete

"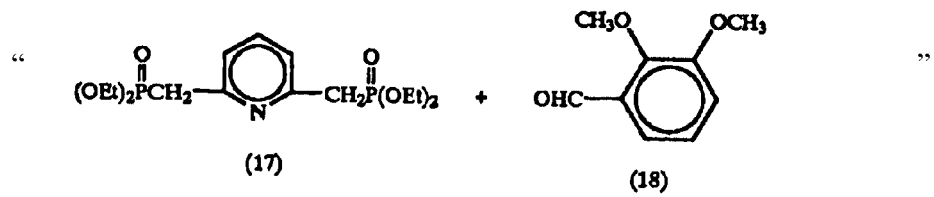"

and insert

--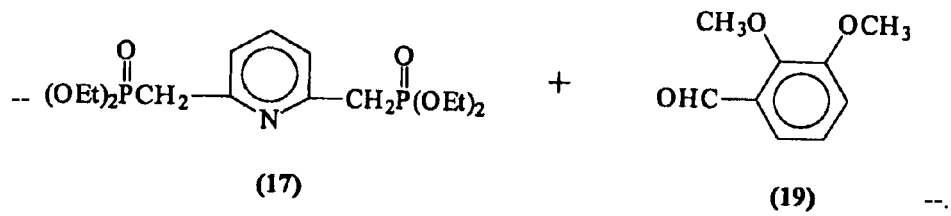--.

Signed and Sealed this

Fourth Day of March, 2008

JON W. DUDAS
*Director of the United States Patent and Trademark Office*